United States Patent [19]

Kondou et al.

[11] Patent Number: 5,683,889
[45] Date of Patent: Nov. 4, 1997

[54] REAGENT FOR MEASUREMENT OF MAGNESIUM ION

[75] Inventors: Hitoshi Kondou, Kyoto; Kazuhiko Nagata, Nagaokakyo; Kazue Kawahara, Uji, all of Japan

[73] Assignees: Iatron Laboratories, Inc., Tokyo; Unitika, Ltd., Hyogo, both of Japan

[21] Appl. No.: 960,364

[22] PCT Filed: Mar. 9, 1992

[86] PCT No.: PCT/JP92/00278

§ 371 Date: Sep. 23, 1993

§ 102(e) Date: Sep. 23, 1993

[87] PCT Pub. No.: WO92/16650

PCT Pub. Date: Oct. 1, 1992

[30] Foreign Application Priority Data

Mar. 14, 1991 [JP] Japan .................................. 3-075720

[51] Int. Cl.$^6$ .................................. C12Q 1/54; C12Q 1/00
[52] U.S. Cl. .................................. 435/14; 435/4
[58] Field of Search .................. 435/14, 4, 194, 435/814

[56] References Cited

U.S. PATENT DOCUMENTS 4,623,625  11/1986  Scopes ............................. 435/190
4,778,754  10/1988  Murachi ........................... 435/14

FOREIGN PATENT DOCUMENTS

WO84/04329  11/1984  WIPO.

OTHER PUBLICATIONS

Scopes, et al., The Biochemical Journal, "Simultaneous purification and characterization of glucokinase, fructokinase and glucose–6–phosphate dehydrogenase from *Zymomonas mobillis*", vol. 228, No. 3, pp. 627–634, Jun. 15, 1985.

*Primary Examiner*—Ralph Gitomer
*Attorney, Agent, or Firm*—Wenderoth, Lind & Ponack

[57] ABSTRACT

The present invention relates to a reagent for measurement of magnesium ions utilizing a complex of magnesium ion with adenosine 5'-triphosphate as a substrate of glucokinase derived from bacteria of the genus Zymomonas. By using this reagent, enough measuring range to measure a magnesium ion in various samples such as biological fluids, foodstuffs, etc. can be accomplished and, at the same time, the measurement can be made with high precision and reliability even in a sample containing a magnesium ion in low concentration. Further, the reagent of the present invention is superior in operation property by reducing a dilution operation, and has sufficient performance for a routine method for determination of magnesium ions.

4 Claims, 1 Drawing Sheet

5,683,889

REAGENT FOR MEASUREMENT OF MAGNESIUM ION

TECHNICAL FIELD

The present invention relates to a reagent for measurement of the content of magnesium ions in various samples, which is useful for the fields of medical sciences, food analysis and environmental preservation.

BACKGROUND ART

The measurement of magnesium ions in biological fluids (e.g. blood, etc.), foods, the environment, such as rivers, and the like has widely been made, and is considered to be important. Methods for measuring magnesium ions are classified into a an instrumental analysis method (e.g. atomic absorption spectrophotometry, etc.) and by a chemical method (e.g. xylidyl blue method, etc.). According to the former method, comparatively accurate results can be obtained. However, expensive instruments are especially required and operation is complicated, whereby, great skill is required. Further, the latter method is a simple method, however, it has a problem that results including large error factors are obtained because it lacks specificity to magnesium ions and the influence of coexisting substances in the sample can not be avoided.

In order to solve these problems, there has been proposed various reagents for the measurement of magnesium ions which utilize an enzyme reaction. These reagents are those which utilize the fact that various kinases enzymes such as hexokinase (hereinafter abbreviated as HK) act on a complex of a magnesium ion with adenosine 5'-triphosphate (hereinafter abbreviated as ATP) as a substrate to manifest their activities. Examples thereof include reagents utilizing a coupling reaction of HK with glucose-6-phosphate dehydrogenase (hereinafter abbreviated as G6PDH) [Methods of Enzymatic Analysis, 3rd edition, pages 592–597, 1985: U.S. Pat. No. 4,657,854]; reagents utilizing a coupling reaction of glucokinase (hereinafter abbreviated as GlcK) having high specificity to glucose, which is similar to HK in the enzymatic reaction, with G6PDH [summaries of the 25th annual meeting of Japan Society of Clinical Chemistry, page 75, 1985: U.S. Pat. No. 4,778,754]; reagents utilizing a coupling reaction of three enzymes, glycerol kinase (hereinafter abbreviated as Glyk), glycerol-3-phosphate dehydrogenase (hereinafter abbreviated as G3PDH) and peroxidase (hereinafter abbreviated as POD) [Clinical Chemistry, Vol. 32, pages 629–632, 1986] and the like. In WO88/08137, there is described an adenylate kinase or HK which is sensitive to a magnesium ion which can be used, however, there is no disclosure about the accuracy of such measurements.

The composition for measurement utilizing these enzyme reactions is provided in light of the chemical method and accuracy of the measurement. However, ATP can form a complex with divalent metal ions (e.g. manganese, calcium, zinc, etc.) in addition to magnesium and the complex can also be a substrate of an enzyme and, therefore, there is a risk that error will occur upon determination of magnesium ions or when a large amount of these metal ions are also present in a sample.

On the contrary, there has also been proposed that these error factors are avoided by masking a divalent metal ion other than a magnesium ion with a chelating agent (see Japanese Patent Kokai No. 1-51100).

Among various enzymatic measuring methods, a method utilizing a coupling reaction of GlcK with G6PDH is most practical from the viewpoints of stability of the reagent, accuracy of the measurement and the like. However, in this method, measuring range is comparatively narrow, particularly when a sample containing a magnesium ion in high concentration is used, which requires dilution of a sample whenever the measurement is made making the measurement complicated. Therefore, regarding a sample containing a magnesium ion in high concentration such as urea and the like, measurement errors are caused by the complicated operation.

DISCLOSURE OF THE INVENTION

The object of the present invention is to provide a reagent for measurement of magnesium ions, which has a measuring range wherein the determination can be made without dilution even in a sample containing high concentration of magensium ions.

The present inventors have studied intensively for the purpose of providing a composition for measurement of a magnesium ion which satisfies the above requirements. As a result, it has been found that the above object is accomplished by using GlcK derived from bacteria of the genus Zymomonas as GlcK and the composition for measurement of a magnesium ion of the present invention is a composition for measurement having enough performance to be usually used, and the present invention has been completed.

That is, according to the present invention, there is provided a reagent for measurement of magnesium ions wherein the magnesium ion is allowed to form a complex with adenosine 5'-triphosphate and then quantitative determination is made by employing the complex as a substrate of an enzyme reaction, characterized in that glucokinase derived from bacteria of the genus Zymomonas is used.

The reagent for measurement of a magnesium ion comprises ATP, nicotinamide adenine dinucleotide (phosphate) (hereinafter abbreviated as NAD(P)) and glucose as a main ingredient, in addition to the above GlcK and G6PDH and, further, it can also contain additives such as chelating agents, accelerators, excipients, preservatives and the like.

Each concentration of the main ingredients in the reagent of the present invention is as follows. The concentration of GlcK, G6PDH, ATP, NAD(P) and glucose is 0.1 to 50 units/ml, 0.1 to 50 units/ml, 0.01 to 20 mM, 0.1 to 20 mM and 1 to 100 mM, respectively. Preferably, the concentration of Glck, G6PDH, ATP, NAD(P) and glucose is 0.1 to 10 units/ml, 0.2 to 10 units/ml, 0.05 to 10 mM, 0.2 to 10 mM, 1 to 50 mM, respectively. The concentration of the chelating agent is preferably about 0.001 to 10 mM. The concentration of the salts is preferably about 1 to 300 mM.

GlcK used in the present invention must be those derived from a bacteria of the genus Zymomonas. The origin of GlcK is not limited to a specific one and examples thereof include bacteria of the genus Zymomonas such as *Zymomonas mobilis*, *Zymomonas anaerobia* and the like. Among them, GlcK derived from bacteria of the genus *Zymomonas mobilis* is particularly preferred. Examples thereof include *Zymomonas mobilis* ATCC strains, 31821, 31823, 35000, 35001, 10988, 29191, 29129 and the like.

In order to obtain GlcK from the above bacteria of the genus Zymomonas, bacteria is cultured on a culture medium which is normally used for culturing, followed by isolating and purifying from the resulting cells by a conventional method.

In the present invention, G6PDH is also used as a coupling enzyme, in addition to GlcK. However, the origin breed of G6PDH is not limited to a specific one (e.g.

microorganisms such as yeast, animals, etc.). Preferably, as the coenzyme, there is G6PDH which acts on nicotinamide adenine dinucleotide (hereinafter abbreviated as NAD) as well as NAD(P) [e.g. those derived from microorganisms that belong to the genus Leuconostoc such as *Leuconostoc mesenteroides*, the genus Pseudomonas such as *Pseudomonas fluorescens* or the genus Zymomonas such as *Zymomonas mobilis*, etc.]. More preferably, G6PDH derived from thermophilic bacteria having excellent stability and storage stability, wherein both NAD(P) and NAD can be used as the coenzyme is preferable.

The chelating agent may be those in which there is a numerical difference of two or more in a chelate stability constant between magnesium and other divalent metal ions [see Rikagaku Jiten, 3rd edition, page 61, 1981, published by Iwanami Shoten; Kagaku Daijiten, 1st edition, pages 496–497, 1963, published by Kyoritsu Shuppan]. The chelate stability constant is usually expressed as a logarithm of an inverse number of dissociation constant of chelate complex with metal ion. Examples thereof include ethylenediaminetetraacetic acid, glycoletherdiamine-N,N,N',N'-teteracetic acid (hereinafter abbreviated as GEDTA), 1,2-bis(O-aminophenoxy)ethane-N,N,N',N'-tetraacetic acid (hereinafter abbreviated as BAPTA), trans-1,2-cyclohexanediamine-N,N,N',N'-tetraacetic acid, dihydroxyethylglycine, ethylenediamine-N,N'-dipropionic acid, hydroxyethyliminodiacetic acid, nitrilotriacetic acid and the like.

As the salts, for example, normal salts such as potassium chloride can be used.

In the principle of the measurement according to the present invention, the content of a magnesium ion is not directly determined, but a complex is a once formed between a magnesium ion and ATP and then the enzyme reaction using the complex as a substrate is utilized. The actual reaction can be shown as follows.

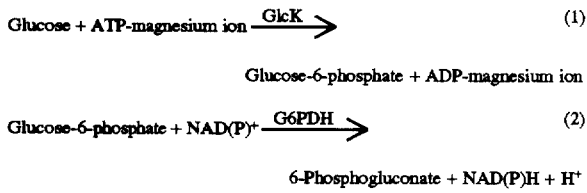

That is, an increasing rate in absorbance at 340 nm due to the formation of NAD(P)H in the above coupling reaction of the formulas (1) and (2) is measured.

In order to measure magnesium ions in a sample using the reagent of the present invention, for example, a reagent for measurement is charged in a cell of a spectrophotometer of which cell chamber is thermally controlled, which is maintained at a measuring temperature (any temperature of 20° to 45° C.) for about 3 minutes, thereafter, a sample is added to mix and then increase in absorbance at 340 nm is measured. Further, the reaction time for the measurement after the addition of the sample can be optionally selected from the range between 30 seconds and 30 minutes. In the case of using an autoanalyser, the condition suitable for the measuring condition of the autoanalyser may be selected.

Most Preferred Embodiment for Working of the Present Invention

The following Examples and Comparative Examples further illustrate the present invention in detail but are not to be construed to limit the scope thereof.

Example 1 and Comparative Example 1

*Zymomonas mobilis* ATCC29191 was cultured according to a method described in The Biochemical Journal, Vol. 228, pages 627–634, 1985 followed by isolating and purifying GlcK and G6PDH, respectively. It was cultured on a medium wherein biotin (1 mg), calcium pantothenate (2 mg) and ammonium iron sulfate hexahydrate (20 mg) were added to 1 liter of a solution containing 15% glucose, 0.5% yeast extract, 0.05% potassium monophosphate and 0.05% magnesium sulfate.

After culturing, the collected cells were disrupted and allowed to adsorb on a Scarlet MX-G sepharose chromatography (Scarlet MX-G is available from ICI Japan Co. under the trade name of Procion Scarlet MX-G). GlcK was eluted by increasing pH and G6PDH was eluted by adding NAD(P), respectively, and then they were subjected to ammonium sulfate fractionation. Further, both enzymes were subjected to gel filtration on a Sephacryl S-200 chromatography to obtain a purified enzyme. By using GlcK and G6PDH purified as described above, a reagent for measurement of a magnesium ion was prepared. A reagent comprising 1 unit/ml of GlcK, 0.75 units/ml of G6PDH, 2.5 mM ATP [available from Boehlinger Mannheim Yamanouchi Co.], 0.625 mM NAD(P) [available from Boehlinger Mannheim Yamanouchi Co.], 0.5 mM GEDTA, 18.75 mM potassium chloride and 125 mM imidazole-hydrochloric acid buffer solution (pH 8.0) was prepared (Example 1). In addition, a 50 mM glucose solution was also prepared.

For comparison, by using GlcK derived from *Bacillus stearothermophilis* [available from Seikagaku Kogyo Co.] and G6PDH derived from *Leuconostoc mesenteroides* [available from Boehlinger Mannheim Yamanouchi Co.], a reagent for measurement of a magnesium ion having the following composition was prepared (Comparative Example 1, see Japanese Patent Kokai No. 1-51100). A reagent comprising 0.44 units/ml of GlcK, 0.75 units/ml of G6PDH, 12.5 mM ATP, 0.625 mM NAD(P), 0.5 mM GEDTA, 18.75 mM KCl and 125 mM tris-hydrochloric acid buffer solution (pH 8.5) was prepared.

Then, by using magnesium chloride, various solutions having magnesium ion concentrations of 0, 4, 8, 12, 16, 20, 24, 28, 32, 36 and 40 mg/dl were prepared as a sample.

The reagent for measurement prepared above (2.4 ml) was charged in a cell having an optical path length of 1 cm and the sample prepared above (0.03 ml) was added. After a cell chamber was maintained at 37° C., the reaction was initiated by adding a glucose solution (0.6 ml) and change in absorbance at 340 nm was measured to determine a magnesium content in the sample from change in absorbance per one minute. The results are shown FIG. 1.

In Example 1, change in absorbance per one minute linearly increased until about 30 mg/dl of the magnesium content. On the other hand, in Comparative Example 1, change in absorbance per one minute linearly increased until only about 10 mg/dl of the magnesium content. It became clear that the reagent for measurement of the present invention exhibits a wide measuring range.

Example 2

By Using GlcK prepared in Example 1 and G6PDH derived from *Leuconostoc mesenteroides* [available from Boehlinger Mannheim Yamanouchi Co.], a reagent for measurement of a magnesium ion was prepared. A reagent comprising 1 unit/ml of GlcK, 0.75 units/ml of G6PDH, 2.5 mM ATP, 0.625 mM NAD(P), 0.625 mM BAPTA, 18.75 mM potassium chloride and 125 mM imidazole-hydrochloric acid buffer solution (pH 8.0) was prepared (Example 2). According to the same manner as that described in Example 1, each solution having various magnesium content was measured to examine a dependence of change in absorbance per one minute on magnesium content. As a result, it was found that change in absorbance per one minute has a linear relation to the magnesium content until about 30 mg/dl. It was shown that the reagent for measurement of the present invention has a wide measuring range.

Example 3

A reagent similar to that of Example 1 was prepared. By using a serum having the magnesium content of about 0.6 mg/dl as a sample, the same sample was measured 30 times to examine accuracy of the measurement. As a result, a measured average value was 0.61 mg/dl, a standard deviation was 0.01 mg/dl and a coefficient of variation indicating accuracy of the measurement was 1.64%. Therefore, it was shown that it is an extremely accurate reagent. It was found that the reagent for measurement of the present invention has wide measuring range and, at the same time, it is a reagent by which accurate measuring can be made even at low concetration range of a magnesium ion.

Example 4

A reagent similar to that of Example 2 was prepared and stored in a refrigerator for about one month. By using three kinds of reagents, the magnesium content in each sample was measured every 10 days. The results are shown in Table 1.

TABLE 1

| (Change in measuring range on the storage) | | | | |
|---|---|---|---|---|
| Storage period | Magnesium measured value (mg/dl) | | | |
| of time (days) | 0 | 10 | 20 | 30 |
| Sample 1 | 0.51 | 0.51 | 0.50 | 0.50 |
| Sample 2 | 15.0 | 15.1 | 15.0 | 14.9 |
| Sample 3 | 27.9 | 28.1 | 28.0 | 27.9 |

As described above, it was found that the reagent for measurement of the present invention is a stable reagent of which measuring range is maintained for a long period of time.

Example 5

By using GlcK and G6PDH prepared in Example 1, a reagent for measurement of a magnesium ion was prepared. A reagent comprising 1.0 unit/ml of GlcK, 0.75 units/ml of G6PDH, 12.5 mM glucose, 0.625 mM NAD(P), 0.5 mM GEDTA, 18.75 mM HCl, 12.5 mM N-acetylcysteine and 100 mM Bicine buffer solution (pH 7.8) was prepared. In addition, a reagent comprising 16 mM ATP, 80 mM ammonium sulfate and 20 mM Bicine solution (pH 7.8) was also prepared.

Then, according to the same manner as that described in Example 1, sample solutions having magnesium in concentrations of 0, 4, 8, 12, 16, 20, 24, 28, 32, 36 and 40 mg/dl were prepared, respectively, using magnesium chloride.

The reagent for measurement prepared above (2.4 ml) was charged in a cell having an optical path length of 1 cm and the sample prepared above (0.03 ml) was added. After a cell chamber was maintained at 37° C., the reaction was initiated by adding a reagent containing ATP (0.6 ml). It was found that change in absorbance per one minute at 340 nm linearly increases until about 32 mg/dl of the magnesium content in the sample. It was shown that the reagent for measurement of the present invention exhibits a wide measuring range.

Example 6

By using GlcK prepared in Example 1 and G6PDH derived from *Leuconostoc mesenteroides*, a reagent for measurement of magnesium ion was prepared. A reagent comprising 1 unit/ml of GlcK, 1.5 units/ml of G6PDH, 12.5 mM glucose, 4 mM NAD(P), 0.5 mM GEDTA, 18.75 mM KCl, 12.5 mM N-acetylcysteine and 100 mM Bicine buffer solution (pH 7.8) was prepared. In addition, a reagent comprising 16 mM ATP, 80 mM ammonium sulfate and 20 mM Bicine buffer solution (pH 7.8) was also prepared. These two kinds of reagents were stored in a refrigerator for about one month. By using three kinds of samples containing magnesium, the magnesium content in each sample was measured every 10 days. The results are shown in Table 1.

TABLE 1

| (Change in measuring range on the storage) | | | | |
|---|---|---|---|---|
| Storage period | Magnesium measured value (mg/dl) | | | |
| of time (days) | 0 | 10 | 20 | 30 |
| Sample 1 | 0.50 | 0.50 | 0.49 | 0.50 |
| Sample 2 | 15.1 | 15.0 | 15.0 | 15.1 |
| Sample 3 | 28.0 | 28.1 | 27.9 | 27.9 |

As described above, it was found that the reagent for measurement of the present invention is a stable reagent of which measuring range is maintained for a long period of time.

Example 7

By using GlcK prepared in Example 1 and G6PDH derived from *Leuconostoc mesenteroides*, a reagent for measurement of magnesium ion was prepared. A reagent comprising 1 unit/ml of GlcK, 1.5 units/ml of G6PDH, 12.5 mM glucose, 4 mM NAD(P), 0.5 mM GEDTA, 18.75 mM KCl, 20 mM ammonium sulfate, 12.5 mM N-acetylcysteine and 100 mM Bicine buffer solution (pH 7.8) was prepared. In addition, a reagent comprising 16 mM ATP and 20 mM Bicine buffer solution was also prepared.

Then, each solution having the magnesium content of 0.5 mg/dl, 10 mg/dl or 30 mg/dl is prepared, respectively, and the same sample was measured 30 times to examine accuracy of the measurement. As a result, a measured average value was 0.51 mg/dl, 10.1 mg/dl and 29.9 mg/dl; a standard deviation was 0.01 mg/dl, 0.15 mg/dl and 0.30 mg/dl; and a coefficient of variation indicating accuracy of the measurement was 1.06%, 1.49% and 1.00%, respectively. Therefore, it was shown that it is extremely accurate reagent. It was found that the reagent for measurement of the present invention has wide measuring range and, at the same time, it is a reagent by which accurate measuring can be made even at low concentration range of a magnesium ion.

Figure 1:
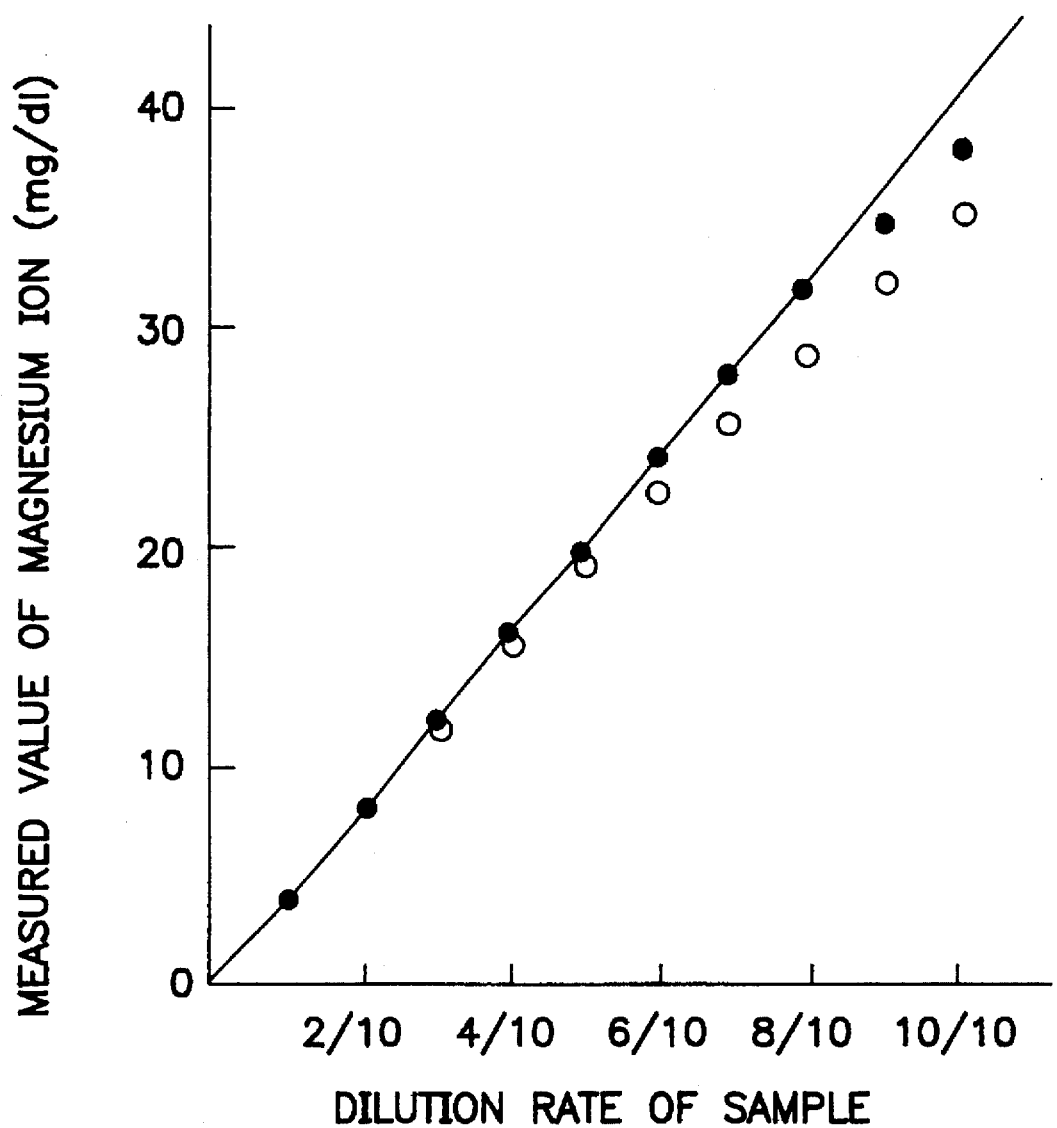
FIG. 1 is a graph showing a measuring range of the reagent for measurement of a magnesium ion of the present invention, wherein ordinates indicate a measured value of the magnesium ions (mg/dl) in a sample and abscissas indicate a dilution rate of a sample. A mark (●) indicates the measured results of Example 1 and a mark (○) indicates those of Comparative Example 1.

We claim:

1. A reagent for substantially linearly measuring magnesium ions at a concentration range 0 to about 32 mg/dl comprising 0.01 to 20 mM adenosine 5'-triphosphate (ATP), 0.1 to 50 units/ml of glucose-6-phosphate dehydrogenase, 0.1 to 20 mM nicotinamide adenine dinucleotide phosphate, 1 to 100 mM glucose and 0.1 to 50 units/ml of glucokinase isolated from the bacterial genus Zymomonas, wherein the magnesium ions are complexed with ATP to form a glucokinase substrate for quantitative determination of magnesium ions, said reagent having good storage stability.

2. The reagent for measuring magnesium ions according to claim 1, wherein glucokinase is isolated from *Zymomonas mobilis*.

3. A method for substantially linearly measuring magnesium ions at a concentration range between 0 and about 32 mg/dl comprising, complexing magnesium ions with 0.01 to 20 mM of adenosine 5'-triphosphate (ATP) to form an Mg-ATP complex, reacting the Mg-ATP complex with 1 to 100 mM of glucose and 0.1 to 50 units/ml of glucokinase isolated from Zymomonas bacteria to form glucose-6-phosphate and reacting the glucose-6-phosphate with 0.1 to 20 mM of nicotinamide adenine dinucleotide (phosphate) NAD (P) and 0.1 to 50 units/ml of glucose-6-phosphate dehydrogenase to form a composition comprising a 6-phosphogluconate and a reduced form of NAD(P) while measuring the increase in absorbance of the composition at 340 nm due to formation of NAD(P)H, thereby indirectly determining the amount of magnesium ions therein.

4. A method for substantially linearly measuring magnesium ions at a concentration range between 0 and about 32 mg/dl comprising reacting a sample containing magnesium ions with a reagent comprising 0.1 to 50 units/ml of glucokinase isolated from Zymomonas bacteria, 0.1 to 50 units/ml of glucose-6-phosphate dehydrogenase, 0.01 to 20 mM adenosine 5'-triphosphate, 0.1 to 20 mM nicotinamide adenine dinucleotide phosphate and 1 to 100 mM glucose and measuring the increase in absorbance of the thus reacted sample at 340 nm due to formation of NAD(P)H, thereby indirectly determining the amount of magnesium ions in the sample.

* * * * *